United States Patent
Song

(10) Patent No.: US 8,912,356 B2
(45) Date of Patent: Dec. 16, 2014

(54) DCC MEDIATED COUPLING FOR HALOFENATE MANUFACTURE

(71) Applicant: Metabolex, Inc., Hayward, CA (US)

(72) Inventor: Jiangao Song, Sunnyvale, CA (US)

(73) Assignee: Cymabay Therapeutics, Inc., Newark, CA (US)

( * ) Notice: Subject to any disclaimer, the term of this patent is extended or adjusted under 35 U.S.C. 154(b) by 0 days.

(21) Appl. No.: 13/745,315

(22) Filed: Jan. 18, 2013

(65) Prior Publication Data

US 2014/0206892 A1 Jul. 24, 2014

(51) Int. Cl.
C07C 231/02 (2006.01)
(52) U.S. Cl.
CPC .................................. *C07C 231/02* (2013.01)
USPC .......................................................... 560/62
(58) Field of Classification Search
None
See application file for complete search history.

(56) References Cited

U.S. PATENT DOCUMENTS 7,432,394 B2 10/2008 Cheng et al.
2010/0093854 A1 4/2010 Broggini et al.

OTHER PUBLICATIONS

Steglich et al. Angew. Chem. Int. Ed. 1978, 7, 522-524.*

* cited by examiner

*Primary Examiner* — Brandon Fetterolf
*Assistant Examiner* — Ana Z Muresan
(74) *Attorney, Agent, or Firm* — Sam L. Nguyen; Hamilton, DeSanctis & Cha, LLP

(57) ABSTRACT

The present application discloses a process for the preparation of a halofenate compound of the formula (III) or a salt thereof:

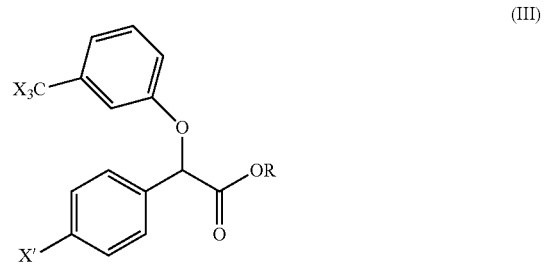

(III)

wherein R, X and X' are as defined herein, the process comprising contacting a compound of formula (Ia) with a compound of formula (Ib) and N,N'-dicyclohexylcarbodiimide under conditions sufficient to form the compound of formula (III).

20 Claims, No Drawings

DCC MEDIATED COUPLING FOR HALOFENATE MANUFACTURE

Ester and amide derivatives of (−)-4-chloro-α-(3-trifluoromethylphenoxy)phenylacetic acid (I) ((−)-halofenic acid), including (−)-halofenate (II), are chiral compounds and are useful in ameliorating a variety of physiological conditions, including conditions associated with blood lipid deposition, Type II diabetes, hyperlipidema and hyperuricemia (see, e.g., U.S. Pat. Nos. 7,199,259 and 6,262,118 which are incorporated herein by reference in their entireties).

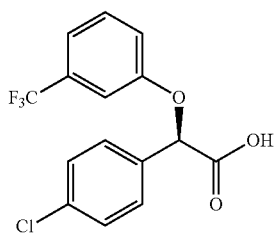

(I)

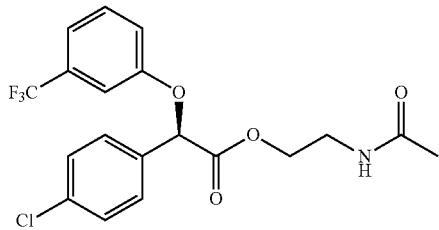

(II)

Halofenic acid and its ester and amide derivatives contain a single chiral center alpha to the carbonyl carbon atom, and therefore exist in two enantiomeric forms. The administration of halofenate (i.e., a racemic mixture of the two enantiomers of 2-acetamidoethyl (4-chlorophenyl) (3-trifluoromethylphenoxy)acetate) results in lowering plasma glucose, triglycerides and serum uric acid. However, this racemic mixture also results in various adverse effects including nausea, gastrointestinal ulcers, and gastrointestinal bleeding. Other side effects that have been reported with racemic halofenate include potential adverse drug-drug interactions, including difficulties controlling anticoagulation with Coumadin™. It has been determined that the (−)-enantiomer of halofenic acid is about twenty-fold less active in its ability to inhibit cytochrome P450 2C9 compared to the (+)-enantiomer. It is therefore more desirable and advantageous to administer the (−)-enantiomer of halofenate instead of racemic halofenate.

Various synthetic routes for preparing (−)-halofenic acid derivatives, such as (−)-halofenate, have been reported in literature. However, these derivatives are often difficult to prepare in high yields and high enantiomeric purity using known synthetic methods. Therefore, there is a need for a process for preparing α-(phenoxy)phenylacetic acid and derivatives thereof, such as (−)-halofenate, with high yields and high enantiomeric purity.

One aspect provides for a process for the preparation of a compound of the formula (III) or a salt thereof:

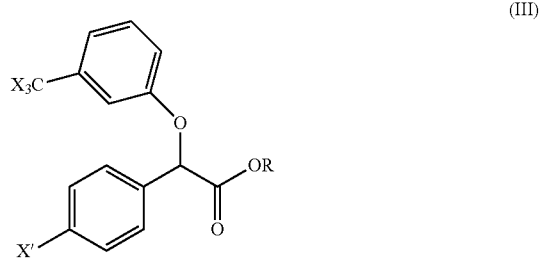

(III)

wherein:
R is selected from the group consisting of aryl$C_{1-6}$alkyl-, $(C_{1-6}alkyl)_2NC_{1-6}$alkyl-, $C_{1-6}$alkyl-NHC$_{1-6}$alkyl-, $C_{1-6}$alkylC(O)NHC$_{1-6}$alkyl-, arylC(O)NHC$_{1-6}$alkyl-, $C_{1-6}$alkyl-NHC(O)NHC$_{1-6}$alkyl-, aryloxyC$_{1-6}$alkyl- and $C_{1-6}$alkylNHC(O)NHphenyl-; and
X and X' are each independently a halogen;
the process comprising:
contacting a compound of the formula (Ia)

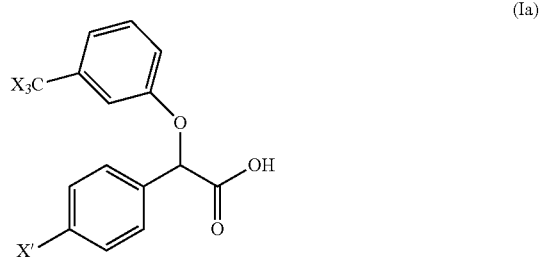

(Ia)

wherein X and X' are each independently a halogen;
with a compound of formula (Ib)

ROH                                     (Ib)

wherein R is defined above; and
a coupling agent;
in an aprotic solvent under conditions sufficient to form the compound of formula (III).

In one embodiment, the compound of formula (III) obtained from the crude reaction mixture (i.e. obtained before recrystallization) may be allowed to remain in the crude reaction mixture without requiring workup for an extended period of time, wherein the compound of the formula (III) does not undergo epimerization or racemization. For example, the compound of the formula (III) may remain in the crude reaction mixture for at least 1.5 hours, 2 hours, 5 hours, 10 hours, 15 hours, 17 hours or more than 24 hours without any measurable racemization. In another embodiment, the compound of the formula (III) may remain in the crude reaction mixture at about 0° C., 10° C., 15° C., 20° C. or at about room temperature for the above cited period of time without any measurable racemization.

In another embodiment, R is $C_{1-6}$alkylC(O)NHC$_{1-6}$alkyl or arylC(O)NHC$_{1-6}$alkyl, X is F and X' is Cl, and the coupling agent is N,N'-dicyclohexylcarbodiimide. In another embodiment, R is CH$_3$CONHCH$_2$CH$_2$— and X is F and X' is Cl. In another embodiment, the compound of the formula (Ib) is N-acetylethanolamine. In another embodiment, no base is used. In another embodiment, the compound of formula (III) is the compound of formula (II):

(II)

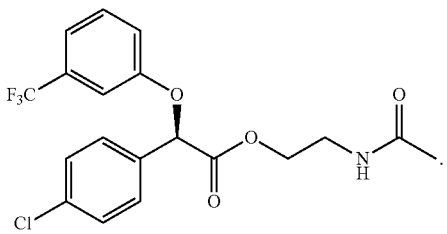

In another embodiment, the aprotic solvent is selected from the group consisting of toluene, xylenes, cyclohexane, diisopropylether, isopropyl acetate, THF, hexanes, MTBE, and combinations thereof. In one variation of the process, the aprotic solvent is toluene. In another embodiment, the mole ratio of N,N'-dicyclohexylcarbodiimide to the compound of formula (Ia) is 1.05:1 to 1.15:1, and the mole ratio of the compound of formula (Ib) to the compound of formula (Ia) is 1.02:1 to 1.7:1. In one variation of the process, the mole ratio of N,N'-dicyclohexylcarbodiimide to the compound of formula (Ia) is 1.1:1, and the mole ratio of the compound of formula (Ib) to the compound of formula (Ia) is 1.5:1. In one embodiment, the process is performed using 4-(N,N-dimethylamino)pyridine (DMAP). In another embodiment, no DMAP is used. In another embodiment, the process is performed with no N-hydroxy based agent typically used in DCC coupling reactions to avoid racemization (such as, e.g., 1-hydroxybenzotriazole (HOBt), N-hydroxysuccinimide (HOSu), or N-hydroxy-5-norbornene-endo-2,3-dicarboximide (BONB)).

In one embodiment, the process further comprises: contacting a compound of formula (Ia) with a compound of formula (Ib); cooling the resulting solution at about 0° C.; and contacting a solution of N,N'-dicyclohexylcarbodiimide with the solution comprising the compounds of formulae (Ia) and (Ib) for a sufficient period of time to form the compound of formula (III). For example, one process comprises contacting a solution comprising N-acetylethanolamine in toluene with a solution of the compound of formula (Ia) in toluene; cooling the resulting solution at about 0° C.; and contacting a solution of N,N'-dicyclohexylcarbodiimide in toluene with the solution comprising N-acetylethanolamine and the compound of formula (Ia) for a sufficient period of time to form the compound of formula (III).

In one embodiment, the process further comprises isolating dicyclohexylurea (DCU) precipitate as a by-product from the filtrate and washing the precipitate with an aprotic solvent such as toluene. In another embodiment, the process further comprises adding an aprotic solvent, such as cyclohexane, to the filtrate, washing the filtrate with water and azeotropically distilling water from the filtrate, and isolating the compound of the formula (III) by crystallization.

In certain embodiments, the compound of formula (III) is obtained with a yield of about 80% or greater before recrystallization. In certain embodiments, the compound of formula (III) is obtained with an enantiomeric excess of about 98% or greater before recrystallization. In various embodiments, the compound of formula (III) has an enantiomeric excess of about 98%, about 99%, about 99.5%, about 99.9%, or greater before recrystallization. In certain embodiments, the compound of formula (III) is obtained with a chemical purity of about 98% or greater before recrystallization. In some embodiments, the compound of formula (III) has a DCU level of less than 1.0% before recrystallization, less than about 0.9%, less than about 0.7%, less than about 0.5%, less than about 0.3% or less than about 0.1%.

In one embodiment, the process provides for the preparation of (−)-halofenate (II) or a salt thereof:

(II)

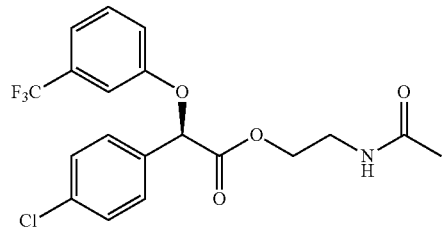

the process comprising: contacting a solution of (−)-4-chlorophenyl-(3-trifluoromethyl-phenoxy)-acetic acid in an aprotic solvent with N-acetylethanolamine; contacting the resulting solution mixture with a solution of N,N'-dicyclohexylcarbodiimide in an aprotic solvent to form (−)-halofenate. In one aspect of the process, the aprotic solvent is selected from the group consisting of toluene, xylenes, cyclohexane, di-isopropyl ether, isopropyl acetate, THF, hexanes and MTBE or combinations thereof. In another aspect, the aprotic solvent is toluene. In another aspect of the process, the contacting the resulting solution mixture with a solution of N,N'-dicyclohexylcarbodiimide in an aprotic solvent s performed at about 0° C. In another aspect, the process further comprises filtering the DCU by-product from the solution.

In certain embodiments, the (−)-halofenate is obtained with a yield of about 80% or greater. In certain embodiments of the process, the (−)-halofenate is obtained with an enantiomeric excess of about 98% or greater before purification, that is, before any purification step (e.g. recrystallization) is performed (that is, as the solid is first obtained from the reaction mixture). In various embodiments, the (−)-halofenate has an enantiomeric excess of about 98%, about 99%, about 99.5%, about 99.9%, or greater before purification. In certain embodiments of the process, the (−)-halofenate is obtained with a chemical purity of about 98% or greater before purification. In some embodiments of the process, the (−)-halofenate has a DCU level of less than 1.0%, about 0.5% about 0.3% or about 0.1% before purification.

In another aspect, the process further comprises purifying (e.g. recrystallizing) the compound of formula (III) (e.g. the compound of formula (II), (−)-halofenate). Recrystallization may be performed in a variety of solvents, for example using diisopropylether, cyclohexane, or a mixture of toluene and cyclohexane. Recrystallization may be used to improve the enantiomeric excess or chemical purity of the desired product. For example, in some embodiments the compound of formula (III) has an enantiomeric excess of about 99.9% or greater after recrystallization. In some embodiments, the compound of formula (III) has a chemical purity of about 99% or greater after recrystallization. In some embodiments, the compound of formula (III) has a DCU level of less than about 0.5%, less than about 0.3%, or less than about 0.1%. Other aspects of the current disclosure are described below.

Unless defined otherwise, all technical and scientific terms used herein have the same meaning as commonly understood by one of ordinary skill in the art. It must be noted that as used herein and in the appended claims, the singular forms "a", "and", and "the" include plural referents unless the context clearly dictates otherwise.

"Alkyl" refers to straight, branched, or cyclic aliphatic hydrocarbons chain groups of one to ten carbon atoms ($C_{1-10}$ alkyl), one to six carbon atoms ($C_{1-6}$ alkyl) or one to four carbon atoms ($C_{1-4}$ alkyl). Exemplary alkyl groups include, but are not limited to, methyl, ethyl, n-propyl, 2-propyl, tert-butyl, pentyl and the like.

"Aryl" refers to a monovalent monocyclic or bicyclic aromatic hydrocarbon moiety of 6 to 10 carbon ring atoms. Unless indicated otherwise, an aryl group can be substituted with one or more substituents, such as one, two or three substituents; or one or two substituents selected from alkyl, haloalkyl, nitro and halo. More specifically the term aryl includes, but is not limited to, phenyl, 1-naphthyl, and 2-naphthyl, and the like, each of which is optionally substituted with one or more substituent(s) noted above.

"Chiral" or "chiral center" refers to a carbon atom having four different substituents. However, the ultimate criterion of chirality is non-superimposability of mirror images.

The terms "CPTA" and "halofenic acid" are used interchangeably herein and refer to (4-chlorophenyl)(3-trifluoromethylphenoxy)acetic acid or 4-chloro-α-(3-trifluoromethylphenoxy)phenylacetic acid. The (−) optical isomer of CPTA has an R configuration at the chiral center, and the (+) optical isomer of CPTA has an S configuration at the chiral center.

"Enantiomeric mixture" refers to a chiral compound having a mixture of enantiomers, including a racemic mixture.

"Enantiomerically enriched" refers to a composition where one enantiomer is present in a higher amount than the other enantiomer.

"Enantiomeric excess" or "% e.e." refers to the amount of difference between the first enantiomer and the second enantiomer. Enantiomeric excess is defined by the equation: % e.e.=(% of the first enantiomer)−(% of the second enantiomer). Thus, if a composition comprises 98% of the first enantiomer and 2% of the second enantiomer, the enantiomeric excess of the first enantiomer is 98%−2% or 96%.

The terms "halogen", "halide" and "halo" are used interchangeably herein and refer to F, Cl, Br and I. In one aspect, halogen refers to F and Cl.

"Haloalkyl" refers to alkyl group as defined herein in which one or more hydrogen atoms have been replaced with halogen(s), including perhaloalkyls, such as trifluoromethyl.

"Halofenate" refers to 2-acetamidoethyl 4-chlorophenyl-(3-trifluoromethyl-phenoxy)acetate (i.e., 4-chloro-α-(3-(trifluoromethyl)phenoxy)benzeneacetic acid, 2-(acetylamino) ethyl ester or (4-chlorophenyl)(3-trifluoromethylphenoxy) acetic acid), 2-(acetylamino)ethyl ester).

Unless otherwise stated, the term "phenyl" refers to an optionally substituted phenyl group. Suitable phenyl substituents are same as those described in the definition of "aryl." Similarly, the term "phenoxy" refers to a group of the formula —OAr$^a$, wherein Ar$^a$ is phenyl as defined herein. Thus, the term "α-(phenoxy)phenylacetic acid" refers to acetic acid that is substituted on the 2-position with an optionally substituted phenyl and optionally substituted phenoxy moieties.

As used herein, the term "treating", "contacting" or "reacting" refers to adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Many organic compounds exist in optically active forms, i.e., they have the ability to rotate the plane of plane-polarized light. In describing an optically active compound, the prefixes R and S are used to denote the absolute configuration of the molecule about its chiral center(s). The prefixes "d" and "l" or (+) and (−) are employed to designate the sign of rotation of plane-polarized light by the compound, with (−) or (l) meaning that the compound is "levorotatory" and with (+) or (d) is meaning that the compound is "dextrorotatory". There is no correlation between nomenclature for the absolute stereochemistry and for the rotation of an enantiomer. For a given chemical structure, these compounds, called "stereoisomers," are identical except that they are mirror images of one another. A specific stereoisomer can also be referred to as an "enantiomer," and a mixture of such isomers is often called an "enantiomeric" or "racemic" mixture. See, e.g., Streitwiesser, A. & Heathcock, C. H., INTRODUCTION TO ORGANIC CHEMISTRY, 2nd Edition, Chapter 7 (MacMillan Publishing Co., U.S.A. 1981).

The terms "substantially free of its (+)-stereoisomer," "substantially free of its (+)-enantiomer," are used interchangeably herein and mean that the compositions contain a substantially greater proportion of the (−)-isomer in relation to the (+)-isomer. In one embodiment, the term "substantially free of its (+) stereoisomer" means that the composition is at least 90% by weight of the (−)-isomer and 10% by weight or less of the (+)-isomer. In another embodiment, the term "substantially free of its (+)-stereoisomer" means that the composition contains at least 99% by weight of the (−)-isomer and 1% by weight or less of the (+)-isomer. In another embodiment, the term "substantially free of its (+)-stereoisomer" means that the composition contains greater than 99%, 99.5%, 99.8% or 99.9% by weight of the (−)-isomer. These percentages are based upon the total amount of isomers in the composition.

In one embodiment, the present application discloses a condensation reaction of (−)-CPTA with N-acetylethanolamine to provide (−)-halofenate in high chemical yields, high chiral purity and provides a favorable by-product profile. In one aspect of the present application, the condensation reaction to provide (−)-halofenate may be performed in a single step.

Coupling reactions using propylphosphonic anhydride (T3P) under a variety of conditions did not provide the desired ester in high yields. It is known that the by-product of T3P can be removed by simple washing with water. Ratios of reagents to (−)-CPTA and different amount of solvents were studied. Reactions were monitored by LC-MS and HPLC. Chiral HPLC methods were used to measure chiral purity (which may be expressed as enantiomeric excess). The coupling reaction could be driven to completion using T3P under optimized conditions, such as increasing the reaction stoichiometry, increasing the concentration of the reactants and elevated reaction temperatures. However, upon completion of the reaction, epimerization of the chiral center invariably resulted under the reaction conditions. Quenching the reaction at 0° C. still resulted in a 50-50 racemic mixture. Bases, such as triethylamine, N,N-diethylisopropylamine and N-methylmorpholine, that have been used in the coupling reaction was thought to be the cause of the racemization. However, in the absence of a base, these coupling reactions did not proceed to completion.

Various other coupling reagents were investigated in the coupling reaction. Base is needed for the reactions when phosphonium (BOP, PyBOP and PyAOP), aminium (HBTU, TBTU, HATU, TATU and HCTU), uronium (TSTU, TNTU, TOTU, TPTU and TDBTU) and the miscellaneous coupling reagents (CIB, CIP, TCFH and DEPBT) were used. Carbodiimides (DCC, DIC and EDC) and imidazolium (CDI) mediated coupling reactions preceded without base. Under various conditions attempted, the CDI coupling reactions did not go to completion. The name of the specific coupling agents are as follows:

| | |
|---|---|
| BOP | Benzotriazole-1-yl-oxy-tris-(dimethylamino)-phosphonium hexafluorophosphate |
| PyBOP | Benzotriazol-1-yl-oxytripyrrolidinophosphonium hexafluorophosphate |
| PyAOP | (7-Azabenzotriazol-1-yloxy)tripyrrolidinophosphonium hexafluorophosphate |
| HBTU | O-Benzotriazole-N,N,N',N'-tetramethyl-uronium-hexafluoro-phosphate |
| TBTU | 2-(1H-Benzotriazole-1-yl)-1,1,3,3-tetramethyluronium tetrafluoroborate |
| HATU | 2-(1H-7-Azabenzotriazol-1-yl)--1,1,3,3-tetramethyl uronium hexafluorophosphate Methanaminium |
| TATU | O-(7-Azabenzotriazole-1-yl)-N,N,N',N'-tetramethyluronium tetrafluoroborate |
| HCTU | 2-(6-Chloro-1H-benzotriazol-1-yl)-1,1,3,3-tetramethylaminium hexafluorophosphate |
| TSTU | N,N,N',N'-Tetramethyl-O-(N-succinimidyl)uronium tetrafluoroborate |
| TNTU | O-(5-Norbornene-2,3-dicarboximido)-N,N,N',N'-tetramethyluronium tetrafluoroborate |
| TOTU | O-[(Ethoxycarbonyl)cyanomethylenamino]-N,N,N',N'-tetramethyluronium tetrafluoroborate |
| TPTU | O-(2-Oxo-1(2H)pyridyl)-N,N,N',N'-tetramethyluronium tetrafluoroborate |
| TDBTU | N,N,N',N'-Tetramethyl-O-(3,4-dihydro-4-oxo-1,2,3-benzotriazin-3-yl)uranium tetrafluoroborate |
| CIB | 2-Chloro-1,3-dimethylimidazolidinium tetrafluoroborate |
| CIP | 2-Chloro-1,3-dimethylimidazolidinium hexafluorophosphate |
| TCFH | N,N,N',N'-Tetramethylchloroformamidinium-hexafluorophosphate |
| DEPBT | 3-(Diethoxyphosphoryloxy)-1,2,3-benzotriazin-4(3H)-one |
| DCC | N,N'-dicyclohexylcarbodiimide |
| DIC | N,N'-diisopropylcarbodiimide |
| EDC | 1-Ethyl-3-(3-dimethylaminopropyl) carbodiimide |
| CDI | Carbodiimidazole |

Typically, the coupling reactions using DCC require a base such as 44N,N-dimethylamino)pyridine (DMAP). However, under certain conditions, the coupling reaction of (−)-halofenic acid with N-acetylethanolamine and DCC resulted in complete conversion to (−)-halofenate without the use of DMAP.

Representative chiral purities (% e.e.) of the coupling products (as crude reaction mixtures) using DCC, DIC and EDC (with and without DMAP) were obtained as follows:

| Coupling Agent/Conditions | % e.e. With DMAP | % e.e. No DMAP |
|---|---|---|
| DCC (0° C.) | 99% | 98% |
| DIC (room temp.) | Not performed | 96% |
| EDC (room temp.) | Not performed | 80% |

In the DCC coupling reaction using a catalytic amount of DMAP, upon the completion of the reaction, the resulting crude reaction mixture was stored over a period of time. Storage of the crude reaction mixture resulted in slow the epimerization of the (−)-halofenate. However, when no DMAP was used in the coupling reaction, there was no further epimerization after the reaction completion. It was noted that the reaction with DMAP was slightly faster than the reaction where DMAP was absent. Upon the completion of the coupling reaction, it was observed that the reaction that was performed without DMAP gave slightly lower chiral purity (98% e.e.) when compared to the coupling reaction performed with DMAP, which afforded a chiral purity of 99% e.e. However, one advantage of performing the reaction without DMAP was that no further epimerization of the resulting product occurring after the reaction was completed such that immediate work-up was not required. Accordingly, DCC may be used in the absence of a base in the ester formation step for the synthesis of (−)-halofenate.

We also studied the effect of the ratio of the coupling reagent to (−)-CPTA on the reaction. A scale-up reaction of 0.1 mol scale of a DCC mediated (−)-CPTA coupling reaction was carried out using the conditions described above. An LC-MS analytical method was developed to determine the residual DCU, a by-product of DCC, in the crude and final product. It was determined that DCU was present at 0.8% in the crude product, and was reduced to 0.48% in the final isolated product after a single recrystallization from diisopropylether.

EXAMPLES

Starting Materials and Reagents (−)-CPTA, Cilag, Lot#07B2213 (>99% e.e.)
N-Acetylethanolamine, Cilag, waxy solid, Lot#07C4811
N-Acetylethanolamine, TCI, viscous liquid, catalog number: A0075, Lot# FI01
DCC, Aldrich, 99%, Lot#13896KMV
DCC Coupling Reactions:

| (−)-CPTA | DCC | N-Acetyl-ethanolamine | DMAP | Toluene | DMA |
|---|---|---|---|---|---|
| 3.3 g | 2.27 g | 2.1 g | 2.5 mg | 5 + 5 mL | 2 mL |
| 1.0 eq | 1.1 eq | 2 eq | 0.2% | | |

DCC in toluene (5 mL) was added to a solution containing (−)-CPTA and N-acetylethanolamine in toluene (5 mL) and DMA (2 mL) via a syringe pump over 20 min at 0° C., and the resulting mixture was stirred at 0° C. for 3 hours.

| Analytical | 3 hours (0° C.) | 1 day, rt | 2 day, rt |
|---|---|---|---|
| Yield (halofenate) | >99% | >99% | >99% |
| Chiral Purity ((−)-halofenate) | 99% e.e. | 97% e.e. | 92.6% e.e. |

The above representative result demonstrates that the coupling reaction using DCC and DMAP provides the desired coupling product. Epimerization of the chiral center occurred slowly over time while the product remained in the reaction mixture. Crude solid from toluene/cyclohexane: 3.45 g, 94.8% e.e. Crystallization from diisopropylether: 2.4 g (recovery yield 70% from crude solid), 96.4% e.e.

When the coupling reaction was performed with dimethylacetamide (DMA), the coupling product was driven to completion, and the product was obtained in high chemical yield, high chiral purity. However, it was determined that the coupling reaction may also be performed without the presence of DMA as a solvent, co-solvent or as an additive to the reaction, and the resulting product was obtained in similar chemical yield and chiral purity.

DCC Coupling Reaction without DMA:

| (−)-CPTA | DCC | N-Acetylethanolamine | DMAP | Toluene |
|---|---|---|---|---|
| 3.3 g | 2.27 g | 2.1 g | 2.5 mg | 5 + 5 mL |
| 1.0 eq | 1.1 eq | 2 eq | 0.2% | |

DDC in toluene (5 mL) was added to the solution via a syringe pump in 20 min at 0° C. and the mixture was stirred at 0° C. for 3 hours.

| Analytical | 30 min (0° C.) |
|---|---|
| Yield (halofenate) | >99% |
| Chiral Purity ((−)-halofenate) | 99% e.e. |

DCC Coupling Reaction without DMAP

| (−)-CPTA | DCC | N-Acetylethanolamine | Base | Toluene |
|---|---|---|---|---|
| 3.3 g | 2.27 g | 2.1 g | None | 7 + 5 mL |
| 1.0 eq | 1.1 eq | 2 eq | None | |

DCC in toluene (5 mL) was added to the solution via a syringe pump in 20 min at 0° C. and the mixture was stirred at 0° C. for 3 hours and at room temperature.

| Analytical | 30 min (0° C.) | 1.5 h (0° C.) | 17 h (rt) | 4 days |
|---|---|---|---|---|
| Yield (halofenate) | 98.9% | >99% | >99% | Not performed |
| Chiral Purity ((−)-halofenate) | ≥98% e.e. | Not performed | 98% e.e. | 98% e.e. |

DCC with Lower Ratio of Reagents:

| (−)-CPTA | DCC | N-Acetylethanolamine | Toluene |
|---|---|---|---|
| 3.3 g | 2.17 g | 1.55 g | 15 mL + 5 mL |
| 1.0 eq | 1.05 eq | 1.5 eq | |

DCC in toluene (5 mL) was added to the solution via a syringe pump in 20 min at 0° C. and the mixture was stirred at 0° C. for 3 hours and at room temperature.

| Analytical | 1.5 h (0° C.) |
|---|---|
| Yield | Halofenate > 99% |
| Chiral Purity ((−)-halofenate) | >98% e.e. |

DCC Using N-Acetylethanolamine from TCI

| (−)-CPTA | DCC | N-Acetylethanolamine | Toluene |
|---|---|---|---|
| 3.3 g | 2.17 g | 1.55 g | 15 mL + 5 mL |
| 1.0 eq | 1.05 eq | 1.5 eq | |

DDC in toluene (5 mL) was added to the solution via a syringe pump in 20 min at 0° C. and the mixture was stirred at 0° C. for 3 hours and at room temperature.

| Analytical | 1.5 h (0° C.) |
|---|---|
| Yield (halofenate) | >99% |

Process Summary:

Scheme 1 illustrates a general method of preparing compounds of formula (III).

Scheme 1

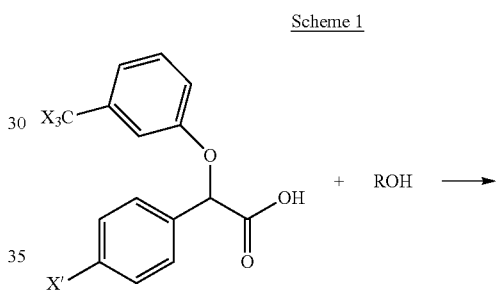

In one embodiment, the process for the preparation of the compound of the formula (III), such as (R)-2-acetamidoethyl 2-(4-chlorophenyl)-2-(3-(trifluoromethyl)phenoxy)acetate, may be performed by initially dissolving DCC in an aprotic solvent, such as toluene. Separately, a solution of ROH, such as N-acetylethanolamine, is dissolved in an aprotic solvent, such as toluene, and the N-acetylethanolamine solution is mixed with a solution of a compound of the formula (Ia) wherein X and X' are as defined herein, such as (−)-CPTA, in an aprotic solvent, such as toluene. Alternatively, a solution of a compound of the formula Ia, such as (−)-4-chloro-phenyl-(3-trifluoromethyl-phenoxy)-acetic acid is prepared in an aprotic solvent, such as toluene, and the compound of the formula ROH, wherein R is as defined herein, is then added to the mixture. The solution of DCC is then added to the solution comprising the compound of the formula (Ia) with the compound of the formula ROH.

In one aspect, the addition of the solution of DCC to the solution comprising the compound of formula (Ia) with ROH is performed below room temperature, such as below about 15° C., below 10° C., below 5° C. or about 0° C. for about 1 hour, 2 hours, 3 hours, 5 hours or more. In one variation, the addition of the DCC solution is performed at about 0° C. for about 1.5 hours or until all of the DCC solution is added.

In another aspect, the resulting solution or suspension is stirred at below room temperature, such as about 10° C. or 0° C., for at least about 3 hours, 5 hours, 7 hours, about 12 hours or more, until the reaction is determined to be complete. Reaction completion may be monitored by chromatographic methods, such as by TLC, HPLC or other spectroscopic methods. The precipitated DCU by-product may be removed from the solution using standard methods, such as filtration over Whatman paper, filtration on a Buchner funnel, optionally with silica gel and/or celite to remove the DCU. Depending on the solvent or solvent mixtures that are used in the process, more than one filtration steps to remove DCU may require as the DCU precipitates out over time. In one variation, the DCU cake is washed with a solvent, such as toluene. To the filtrate contain the product is added an organic solvent, such as cyclohexane, and the resulting solution is washed with water, and water is separated from the organic solution. Residual water is then removed from the organic solution by drying, such as the use of drying agent (sodium sulfate, magnesium sulfate etc.) and or by azeotropic distillation of the cyclohexane-toluene solution.

A solid compound of formula (III), such as (R)-2-acetamidoethyl 2-(4-chlorophenyl)-2-(3-(trifluoromethyl)phenoxy)acetate, may be obtained from solution. In one variation, to the reaction solution is added an organic solvent, such as cyclohexane, and the resulting mixture is heated to above room temperature, such as about 35° C., 37° C. or about 40° C. Optionally, the resulting solution is seeded with crystals of the desired product, such as crystals of (R)-2-acetamidoethyl 2-(4-chlorophenyl)-2-(3-(trifluoromethyl)phenoxy)acetate, and mixed at the same temperature for at least about 1 hour, 2 hours, 3 hours or about 4 hours or more, and the mixture is allowed to cool slowly to room temperature or below room temperature, such for at least about 1 hour, 2 hours, 3 hours or about 4 hours or more, and the resulting crystals are filtered and washed with a cold (about 10° C. or colder) solvent such as cyclohexane. The crystalline product may be dried to afford the desired product.

Different reaction work up conditions, crystallization conditions and isolation conditions using various modifications of the processes as described herein allow the isolation of (−)-halofenate in greater than about 80% yield, greater than about 85% yield, greater than about 90% yield, greater than about 95% yield and greater than about 97% yield. In various aspects, the above described processes allow the isolation of (−)-halofenate at about 98% e.e., about 99% e.e., about 99.5% e.e., about 99.9% e.e. or greater. In various aspects, the above described processes allow the isolated (−)-halofenate to have a DCU level of about 1%, about 0.5%, about 0.4%, about 0.3%, about 0.2%, about 0.1%, about 0.05% or about 0.01% or less. In certain aspects, these e.e. and chemical purity levels are obtained before further purification (e.g. recrystallization) of the compound. In one aspect of the process described herein, the product obtained, (−)-halofenate, is substantially free of its (+)-stereoisomer.

It was determined that, depending on the reaction conditions and the solvent or solvent mixtures employed for each isolation step, DCU may be precipitated out of the solution at different rates over time, and upon precipitation, DCU may be isolated from the desired solution containing the product by a filtration process.

DCC 0.1 Mol of CPTA Reaction, Using N-Acetylethanolamine from TCI

Preparation of (R)-2-acetamidoethyl 2-(4-chlorophenyl)-2-(3-(trifluoromethyl)phenoxy)acetate

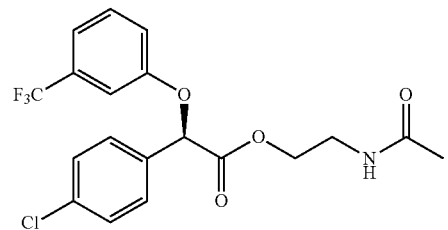

II

DCC (22.7 g, 110 mmol) was dissolved in toluene (50 mL) at 20° C. To a 500 mL of round-bottom flask were added N-acetylethanolamine (15.5 g, 150 mml), toluene (150 mL) and (−)-4-chloro-phenyl)-(3-trifluoromethyl-phenoxy)-acetic acid (33.1 g, 100 mmol). The mixture was stirred at 20° C. until a clear solution was formed. The solution was cooled with an ice-water bath. To the solution was added DCC in toluene solution dropwise at 0° C. in 90 min. The resulted suspension was stirred at 0° C. for 3 hours and then 20° C. over night. Dicyclohexylurea (DCU, obtained as by product) was filtered off and washed with toluene (25 mL) two times. To the filtrate (containing the desired product, (−)-halofenate) was added cyclohexane (100 mL). The solution was washed with water (100 mL) three times. The residual water was removed by azeotropic distillation with cyclohexane and toluene (about 180 mL). To the resulting solution was added cyclohexane (200 mL) at 40° C. and seeded with (−)-halofenate (33 mg). The resulting suspension was stirred at 40° C. for 2 hours, then cooled to 10° C. over 1 hour and stirred for an additional 1 hour. The precipitated crystals were filtered and washed with cold (<10° C.) cyclohexane. The wet product was dried under vacuum over night to yield the title compound as a white solid. Yield: 35.4 g (80.5%), % e.e. 99.5%; chemical purity 98.6% (DCU 0.80%).

The dry solid (35 g) was recrystallized from diisopropylether (350 mL) to give the title compound as a white crystalline solid. Yield: 28.5 g (81.4%), e.e. 99.9%; chemical purity 99.3% (DCU 0.48%).

While the foregoing description describes specific embodiments, those with ordinary skill in the art will appreciate that various modifications and alternatives can be developed. Accordingly, the particular embodiments and examples described above are meant to be illustrative only, and not to limit the scope of the invention, which is to be given the full breadth of the appended claims, and any and all equivalents thereof.

What is claimed is:

1. A process for preparing a compound of formula (IV)

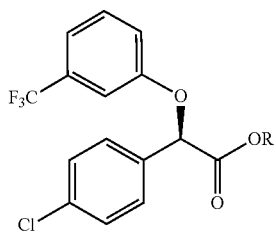

(IV)

where R is $C_{1-6}$alkylC(O)NHC$_{1-6}$alkyl or arylC(O)NHC$_{1-6}$alkyl, comprising the step of contacting (−)-halofenic acid with a compound of the formula ROH and N,N'-dicyclohexylcarbodiimide in an aprotic solvent in the absence of base under conditions sufficient to form the compound of formula (IV).

2. The process of claim 1 where the step is carried out in the absence of an N-hydroxy based agent.

3. The process of claim 1 where the aprotic solvent is selected from the group consisting of toluene, xylenes, cyclohexane, di-isopropyl ether, isopropyl acetate, tetrahydrofuran, hexanes, methyl tert-butyl ether, and combinations thereof.

4. The process of claim 3 where the aprotic solvent is toluene.

5. The process of claim 1 where the mole ratio of N,N'-dicyclohexylcarbodiimide to (−)-halofenic acid is 1.05:1 to 1.15:1, and the mole ratio of the compound of the formula ROH to (−)-halofenic acid is 1.02:1 to 1.7:1.

6. The process of claim 5 where the mole ratio of N,N'-dicyclohexylcarbodiimide to (−)-halofenic acid is 1.1:1, and the mole ratio of the compound of the formula ROH to (−)-halofenic acid is 1.5:1.

7. A process for the preparation of (−)-halofenate, comprising the step of contacting (−)-halofenic acid with N-acetylethanolamine and N,N'-dicyclohexylcarbodiimide in an aprotic solvent in the absence of base under conditions sufficient to form the (−)-halofenate.

8. The process of claim 7 where the step is carried out in the absence of an N-hydroxy based agent.

9. The process of claim 8 where the aprotic solvent is selected from the group consisting of toluene, xylenes, cyclohexane, di-isopropyl ether, isopropyl acetate, tetrahydrofuran, hexanes, methyl tert-butyl ether, and combinations thereof.

10. The process of claim 9 where the aprotic solvent is toluene.

11. The process of claim 7 where the mole ratio of N,N'-dicyclohexylcarbodiimide to (−)-halofenic acid is 1.05:1 to 1.15:1, and the mole ratio of N-acetylethanolamine to (−)-halofenic acid is 1.02:1 to 1.7:1.

12. The process of claim 11 where the mole ratio of N,N'-dicyclohexylcarbodiimide to (−)-halofenic acid is 1.1:1, and the mole ratio of N-acetylethanolamine to (−)-halofenic acid is 1.5:1.

13. A process for the preparation of (−)-halofenate, comprising the steps of:
    contacting a solution comprising N-acetylethanolamine in toluene free of base with a solution comprising (−)-halofenic acid in toluene free of base;
    cooling the resulting solution at about 0° C.;
    contacting a solution of N,N'-dicyclohexylcarbodiimide in toluene free of base with the cooled resulting solution for a sufficient period of time to form (−)-halofenate.

14. The process of claim 13 where the steps are carried out in the absence of an N-hydroxy based agent.

15. The process of claim 14, further comprising the step of separating N,N'-dicyclohexylurea as a precipitate from the (−)-halofenate-containing reaction mixture, leaving a filtrate.

16. The process of claim 15, further comprising the step of washing the precipitate with toluene.

17. The process of claim 15, further comprising the steps of adding cyclohexane to the filtrate, washing the filtrate with water and azeotropically distilling water from the filtrate, and crystallizing and isolating the (−)-halofenate.

18. The process of claim 17 where the isolated (−)-halofenate has an enantiomeric excess of 98% or greater before purification.

19. The process of claim 18 where the isolated (−)-halofenate has an enantiomeric excess of 99% or greater before purification.

20. The process of claim 19 where the isolated (−)-halofenate has an enantiomeric excess of 99.5% or greater before purification.

* * * * *

UNITED STATES PATENT AND TRADEMARK OFFICE
CERTIFICATE OF CORRECTION

| | | |
|---|---|---|
| PATENT NO. | : 8,912,356 B2 | Page 1 of 1 |
| APPLICATION NO. | : 13/745315 | |
| DATED | : December 16, 2014 | |
| INVENTOR(S) | : Jiangao Song | |

It is certified that error appears in the above-identified patent and that said Letters Patent is hereby corrected as shown below:

In the claims
Column 13, lines 16-17:
"$C_{1-6}alkylC(O)NHC_{1-6}alkyl$ or $arylC(O)NHC_{1-6}alkyl$"
should read
-- $C_{1-6}alkylC(O)NHC_{1-6}alkyl$- or $arylC(O)NHC_{1-6}alkyl$- --.

Signed and Sealed this
Fourteenth Day of June, 2016

Michelle K. Lee
*Director of the United States Patent and Trademark Office*